(12) United States Patent
Tadele et al.

(10) Patent No.: US 12,396,686 B2
(45) Date of Patent: Aug. 26, 2025

(54) SENSING HEALTH PARAMETERS IN WEARABLE DEVICES

(71) Applicant: Apple Inc., Cupertino, CA (US)

(72) Inventors: Wegene H. Tadele, San Francisco, CA (US); Maegan K. Spencer, Emerald Hills, CA (US); Riley E. Brandt, Menlo Park, CA (US); Siddharth Nangia, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 268 days.

(21) Appl. No.: 17/899,455

(22) Filed: Aug. 30, 2022

(65) Prior Publication Data
US 2023/0064273 A1 Mar. 2, 2023

Related U.S. Application Data

(60) Provisional application No. 63/239,358, filed on Aug. 31, 2021.

(51) Int. Cl.
*A61B 5/00* (2006.01)

(52) U.S. Cl.
CPC .......... *A61B 5/7203* (2013.01); *A61B 5/6803* (2013.01); *A61B 5/681* (2013.01); *A61B 5/6898* (2013.01); *A61B 2560/0247* (2013.01); *A61B 2562/0204* (2013.01)

(58) Field of Classification Search
CPC ............................. A61B 5/7203; A61B 5/6803
USPC .......................................................... 600/300
See application file for complete search history.

(56) References Cited

U.S. PATENT DOCUMENTS

| 3,355,873 A | 12/1967 | Morf |
| 3,577,876 A | 5/1971 | Spadini |
| 4,015,595 A | 4/1977 | Benjamin, Jr. |
| 4,120,294 A | 10/1978 | Wolfe |

(Continued)

FOREIGN PATENT DOCUMENTS

| AU | 2011252998 | 11/2011 |
| AU | 2014209376 | 7/2014 |

(Continued)

OTHER PUBLICATIONS

Aldinger, F. and Weberruß, V.A., "An Introduction to Structures, Properties, Technologies, Methods" (2010) In: Advanced Ceramics and Future Materials 17 pages.

(Continued)

*Primary Examiner* — Nadia A Mahmood
(74) *Attorney, Agent, or Firm* — Brownstein Hyatt Farber Schreck, LLP

(57) ABSTRACT

Embodiments of this disclosure are directed to a wearable device having a housing, a display, and a sensor system. The display is at least partially surrounded by the housing. The sensor system is housed at least partially in the housing. The sensor system includes a first sensor, a second sensor, and a controller. The first sensor is configured to contact a body part of a user and generate a first signal. The second sensor is configured to sense a mechanical wave in an ambient environment of the wearable device and generate a second signal. The controller is configured to generate a resultant signal by removing noise from the first signal using the second signal, and determine a health parameter of the user from the resultant signal.

15 Claims, 8 Drawing Sheets

(56) References Cited

U.S. PATENT DOCUMENTS

| | | |
|---|---|---|
| 4,129,124 A | 12/1978 | Thalmann |
| 4,163,447 A | 8/1979 | Orr |
| 4,224,948 A | 9/1980 | Cramer et al. |
| 4,248,244 A | 2/1981 | Charnitski et al. |
| 4,274,152 A | 6/1981 | Ikegami |
| 4,375,219 A | 3/1983 | Schmid |
| 4,448,199 A | 5/1984 | Schmid |
| 5,613,008 A | 3/1997 | Martin |
| 5,738,104 A | 4/1998 | Lo et al. |
| 6,075,755 A | 6/2000 | Zarchan |
| 6,091,530 A | 7/2000 | Duckworth |
| 6,198,951 B1 | 3/2001 | Kosuda |
| 6,265,789 B1 | 7/2001 | Honda et al. |
| 6,428,537 B1 | 8/2002 | Swanson et al. |
| 6,529,754 B2 | 3/2003 | Kondo |
| 6,608,562 B1 | 8/2003 | Kimura et al. |
| 6,661,438 B1 | 12/2003 | Shiraishi et al. |
| 6,721,540 B1 | 4/2004 | Hayakawa |
| 6,996,428 B2 | 2/2006 | Kislov et al. |
| 7,187,961 B2 | 3/2007 | Yamashita |
| 7,450,002 B2 | 11/2008 | Choi et al. |
| 7,455,423 B2 | 11/2008 | Takenaka |
| 7,474,592 B2 | 1/2009 | Lyon |
| 7,486,386 B1 | 2/2009 | Holcombe |
| 7,598,878 B2 | 10/2009 | Goldreich |
| 7,646,033 B2 | 1/2010 | Tran et al. |
| 7,652,658 B2 | 1/2010 | Nishi et al. |
| 7,682,070 B2 | 3/2010 | Burton |
| 7,729,748 B2 | 6/2010 | Florian |
| 7,822,469 B2 | 10/2010 | Lo |
| 7,894,888 B2 | 2/2011 | Chan et al. |
| 7,915,601 B2 | 3/2011 | Setlak et al. |
| 7,957,762 B2 | 6/2011 | Herz et al. |
| 8,150,502 B2 | 4/2012 | Kumar et al. |
| 8,160,682 B2 | 4/2012 | Kumar et al. |
| 8,227,887 B2 | 7/2012 | Brown et al. |
| 8,229,535 B2 | 7/2012 | Mensinger |
| 8,244,335 B2 | 8/2012 | Kumar et al. |
| 8,538,503 B2 | 9/2013 | Kumar et al. |
| 8,560,046 B2 | 10/2013 | Kumar et al. |
| 8,562,489 B2 | 10/2013 | Burton et al. |
| 8,624,836 B1 | 1/2014 | Miller et al. |
| 8,670,819 B2 | 3/2014 | Iwamiya et al. |
| 8,758,258 B2 | 6/2014 | Takahashi et al. |
| 8,804,993 B2 | 8/2014 | Shukla et al. |
| 8,824,245 B2 | 9/2014 | Lau et al. |
| 8,842,848 B2 | 9/2014 | Donaldson et al. |
| 8,948,832 B2 | 2/2015 | Hong et al. |
| 8,954,135 B2 | 2/2015 | Yuen et al. |
| 8,988,372 B2 | 3/2015 | Messerschmidt et al. |
| 9,001,625 B2 | 4/2015 | Essery et al. |
| 9,024,250 B2 | 5/2015 | Spraggs |
| 9,030,446 B2 | 5/2015 | Mistry et al. |
| 9,042,971 B2 | 5/2015 | Brumback et al. |
| 9,044,149 B2 | 6/2015 | Richards et al. |
| 9,049,998 B2 | 6/2015 | Brumback et al. |
| 9,100,579 B2 | 8/2015 | Schatvet et al. |
| 9,143,041 B2 | 9/2015 | Itabashi et al. |
| 9,146,304 B2 | 9/2015 | Land et al. |
| 9,173,670 B2 | 11/2015 | Sepulveda et al. |
| 9,241,649 B2 | 1/2016 | Kumar et al. |
| 9,277,880 B2 | 3/2016 | Poeze et al. |
| 9,348,322 B2 | 5/2016 | Fraser et al. |
| 9,427,191 B2 | 8/2016 | LeBoeuf |
| 9,436,645 B2 | 9/2016 | Al-Ali et al. |
| 9,442,570 B2 | 9/2016 | Slonneger |
| 9,451,975 B2 | 9/2016 | Sepulveda et al. |
| 9,485,345 B2 | 11/2016 | Dantu |
| 9,506,802 B2 | 11/2016 | Chu et al. |
| 9,516,442 B1 | 12/2016 | Dusan |
| 9,557,716 B1 | 1/2017 | Inamdar |
| 9,597,004 B2 | 3/2017 | Hughes et al. |
| 9,606,721 B2 | 3/2017 | Park et al. |
| 9,620,312 B2 | 4/2017 | Ely et al. |
| 9,627,163 B2 | 4/2017 | Ely et al. |
| 9,632,537 B2 | 4/2017 | Memering et al. |
| 9,664,556 B2 | 5/2017 | Chu et al. |
| 9,687,165 B2 | 6/2017 | Katra et al. |
| 9,715,301 B2 | 7/2017 | Kuboyama et al. |
| 9,723,997 B1 | 8/2017 | Lamego |
| 9,737,221 B2 | 8/2017 | Sato |
| 9,763,584 B2 | 9/2017 | Freschl et al. |
| 9,772,605 B2 | 9/2017 | Shim et al. |
| 9,775,548 B2 | 10/2017 | Sarantos |
| 9,833,159 B2 | 12/2017 | Chu et al. |
| 9,833,164 B2 | 12/2017 | Justice et al. |
| 9,848,823 B2 | 12/2017 | Raghuram et al. |
| 9,852,844 B2 | 12/2017 | Golko et al. |
| 9,891,098 B2 | 2/2018 | Shedletsky |
| 9,891,590 B2 | 2/2018 | Shim et al. |
| 9,955,887 B2 | 5/2018 | Hughes et al. |
| 9,971,399 B2 | 5/2018 | Lee |
| 10,013,075 B2 | 7/2018 | Shipman |
| 10,058,773 B2 | 8/2018 | Huang |
| 10,060,788 B2 | 8/2018 | Fei |
| 10,092,197 B2 | 10/2018 | Han |
| 10,098,559 B2 | 10/2018 | Hughes et al. |
| 10,123,710 B2 | 11/2018 | Gassoway et al. |
| 10,126,194 B2 | 11/2018 | Lee |
| 10,172,562 B2 | 1/2019 | Lim et al. |
| 10,215,698 B2 | 2/2019 | Han et al. |
| 10,231,629 B1 | 3/2019 | Pei et al. |
| 10,254,804 B2 | 4/2019 | Dusan |
| 10,271,754 B2 | 4/2019 | Bahney et al. |
| 10,271,800 B2 | 4/2019 | Lin et al. |
| 10,299,691 B2 | 5/2019 | Hughes et al. |
| D852,965 S | 7/2019 | Bahney et al. |
| D854,167 S | 7/2019 | Bahney et al. |
| 10,405,799 B2 | 9/2019 | Kumar et al. |
| 10,488,936 B2 | 11/2019 | Baranski |
| 10,517,500 B2 | 12/2019 | Kumar et al. |
| 10,524,671 B2 | 1/2020 | Lamego |
| 10,524,720 B2 | 1/2020 | Newberry |
| 10,534,900 B2 | 1/2020 | Cheong et al. |
| 10,551,929 B2 | 2/2020 | Kim |
| 10,599,101 B2 | 3/2020 | Rothkopf et al. |
| 10,610,157 B2 | 4/2020 | Pandya et al. |
| 10,627,783 B2 | 4/2020 | Rothkopf |
| 10,671,222 B2 | 6/2020 | Kuboyama et al. |
| 10,690,538 B2 | 6/2020 | Lin |
| 10,695,004 B2 | 6/2020 | Gaudet et al. |
| 10,702,211 B2 | 7/2020 | Clavelle |
| 10,716,478 B2 | 7/2020 | Meer et al. |
| 10,761,575 B2 | 9/2020 | Dusan |
| 10,827,268 B2 | 11/2020 | Dusan |
| 10,888,273 B2 | 1/2021 | Myers et al. |
| 10,987,054 B2 | 4/2021 | Pandya et al. |
| 11,024,423 B2 | 6/2021 | Reykhert |
| 11,036,318 B2 | 6/2021 | Kuboyama et al. |
| 11,076,806 B2 | 8/2021 | Townsend et al. |
| 11,123,016 B2 | 9/2021 | Jo et al. |
| 11,166,104 B2 | 11/2021 | Dusan |
| 11,281,262 B2 | 3/2022 | Dusan |
| 11,432,766 B2 | 9/2022 | Clavelle et al. |
| 11,474,483 B2 | 10/2022 | Rothkopf et al. |
| 11,567,457 B2 | 1/2023 | Rothkopf et al. |
| 2001/0056243 A1 | 12/2001 | Ohsaki et al. |
| 2003/0045802 A1 | 3/2003 | Kato |
| 2005/0274971 A1 | 12/2005 | Wang et al. |
| 2006/0069319 A1 | 3/2006 | Elhag et al. |
| 2007/0276270 A1 | 11/2007 | Tran |
| 2008/0208009 A1 | 8/2008 | Shklarski |
| 2009/0265671 A1 | 10/2009 | Sachs et al. |
| 2011/0007468 A1 | 1/2011 | Burton et al. |
| 2011/0015496 A1 | 1/2011 | Sherman et al. |
| 2012/0078116 A1 | 3/2012 | Yamashita |
| 2012/0221254 A1 | 8/2012 | Kateraas et al. |
| 2013/0267854 A1 | 10/2013 | Johnson et al. |
| 2014/0045547 A1 | 2/2014 | Singamsetty et al. |
| 2014/0073486 A1 | 3/2014 | Ahmed et al. |
| 2014/0135594 A1 | 5/2014 | Yuen et al. |
| 2014/0275832 A1 | 9/2014 | Muehlsteff et al. |
| 2014/0343371 A1 | 11/2014 | Sowers et al. |
| 2015/0002088 A1 | 1/2015 | D'Agostino |

(56) References Cited

U.S. PATENT DOCUMENTS

| | | |
|---|---|---|
| 2015/0124415 A1 | 5/2015 | Goyal et al. |
| 2015/0157219 A1 | 6/2015 | Lee et al. |
| 2015/0186609 A1 | 7/2015 | Utter |
| 2015/0195009 A1 | 7/2015 | Wang et al. |
| 2015/0214749 A1 | 7/2015 | Park et al. |
| 2015/0297134 A1 | 10/2015 | Albert et al. |
| 2015/0355604 A1 | 12/2015 | Fraser et al. |
| 2016/0058375 A1 | 3/2016 | Rothkopf |
| 2016/0073914 A1 | 3/2016 | Lapetina et al. |
| 2016/0120472 A1 | 5/2016 | Kub et al. |
| 2016/0198966 A1 | 7/2016 | Uematsu et al. |
| 2016/0228064 A1 | 8/2016 | Jung et al. |
| 2016/0242659 A1 | 8/2016 | Yamashita et al. |
| 2016/0338598 A1 | 11/2016 | Kegasawa |
| 2016/0338642 A1 | 11/2016 | Parara et al. |
| 2017/0049332 A1 | 2/2017 | Park et al. |
| 2017/0164850 A1* | 6/2017 | Murphy ................. A61B 5/742 |
| 2017/0172476 A1 | 6/2017 | Schilthuizen |
| 2017/0296088 A1 | 10/2017 | Choi |
| 2018/0020937 A1 | 1/2018 | Chou |
| 2018/0220972 A1 | 8/2018 | Jeong |
| 2018/0235483 A1 | 8/2018 | Mouradian |
| 2018/0235542 A1 | 8/2018 | Yun et al. |
| 2018/0358119 A1 | 12/2018 | Bhushan et al. |
| 2019/0025438 A1 | 1/2019 | Venkatraman et al. |
| 2019/0090806 A1 | 3/2019 | Harrison-Noonan et al. |
| 2019/0196411 A1 | 6/2019 | Yuen |
| 2019/0209031 A1 | 7/2019 | Ariyama et al. |
| 2020/0000351 A1 | 1/2020 | Rauhala |
| 2020/0100684 A1 | 4/2020 | Lamego |
| 2020/0233381 A1 | 7/2020 | Yang et al. |
| 2021/0181692 A1 | 6/2021 | Rothkopf et al. |
| 2021/0204876 A1 | 7/2021 | Pandya et al. |
| 2023/0028554 A1 | 1/2023 | Rothkopf et al. |
| 2023/0052087 A1 | 2/2023 | Clavelle et al. |
| 2023/0097827 A1 | 3/2023 | Rothkopf et al. |
| 2023/0098960 A1 | 3/2023 | Pandya et al. |
| 2023/0210392 A1 | 7/2023 | Hatanaka et al. |
| 2023/0210461 A1 | 7/2023 | Pandya et al. |
| 2023/0213893 A1 | 7/2023 | Rothkopf et al. |

FOREIGN PATENT DOCUMENTS

| | | |
|---|---|---|
| CH | 188928 | 1/1937 |
| CN | 1572252 | 2/2005 |
| CN | 1985762 | 6/2007 |
| CN | 102246125 | 11/2011 |
| CN | 102483608 | 5/2012 |
| CN | 102867190 | 1/2013 |
| CN | 103191557 | 7/2013 |
| CN | 103645804 | 3/2014 |
| CN | 203564224 | 4/2014 |
| CN | 103919536 | 7/2014 |
| CN | 103956006 | 7/2014 |
| CN | 203693601 | 7/2014 |
| CN | 203732900 | 7/2014 |
| CN | 104050444 | 9/2014 |
| CN | 104510463 | 4/2015 |
| CN | 204515353 | 7/2015 |
| CN | 105339871 | 2/2016 |
| CN | 205041396 | 2/2016 |
| CN | 205121417 | 3/2016 |
| CN | 105556433 | 5/2016 |
| CN | 105955519 | 9/2016 |
| CN | 105980976 | 9/2016 |
| CN | 106236051 | 12/2016 |
| CN | 106388809 | 2/2017 |
| CN | 106462665 | 2/2017 |
| CN | 206209589 | 5/2017 |
| CN | 206324777 | 7/2017 |
| EP | 0165548 | 12/1985 |
| EP | 1981402 | 8/2016 |
| EP | 2568878 | 7/2018 |
| JP | 2001145607 | 5/2001 |
| JP | 2001202178 | 7/2001 |
| JP | 2004028979 | 1/2004 |
| JP | 2005270543 | 10/2005 |
| JP | 2009519737 | 5/2009 |
| JP | 2011021929 | 2/2011 |
| JP | 5477393 | 4/2014 |
| JP | 2014112222 | 6/2014 |
| JP | 2016148657 | 8/2016 |
| KR | 2019950004406 | 5/1995 |
| KR | 200278568 | 6/2002 |
| KR | 1020080028935 | 4/2008 |
| KR | 2020090001515 | 2/2009 |
| KR | 1020090099147 | 9/2009 |
| KR | 20110012784 | 2/2011 |
| KR | 20110103761 | 9/2011 |
| KR | 1020120028314 | 3/2012 |
| KR | 1020130131873 | 12/2013 |
| KR | 1020140051391 | 4/2014 |
| KR | 1020140064689 | 5/2014 |
| KR | 1020140104388 | 8/2014 |
| KR | 1020160041553 | 4/2016 |
| KR | 1020160145284 | 12/2016 |
| KR | 102136836 | 8/2020 |
| TW | 200632604 | 9/2006 |
| TW | 200633681 | 10/2006 |
| TW | 201610621 | 3/2016 |
| TW | 201621491 | 6/2016 |
| TW | 201632136 | 9/2016 |
| WO | WO 82/000088 | 1/1982 |
| WO | WO 05/092182 | 10/2005 |
| WO | WO 12/140559 | 10/2012 |
| WO | WO 13/103570 | 7/2013 |
| WO | WO 15/030712 | 3/2015 |
| WO | WO 15/034149 | 3/2015 |
| WO | WO 15/039373 | 3/2015 |
| WO | WO 15/116111 | 8/2015 |
| WO | WO 15/150199 | 10/2015 |
| WO | WO 16/036747 | 3/2016 |
| WO | WO 16/055853 | 4/2016 |
| WO | WO 16/204443 | 12/2016 |
| WO | WO 17/165532 | 9/2017 |
| WO | WO 18/119193 | 6/2018 |

OTHER PUBLICATIONS

Berbari, E.J., "Principles of Electrocardiology" (2015) In: The Biomedical Engineering Handbook—4th Edition (Eds: J.D. Bronzin & D.R. Peterson) 5 pages.

Canfield, D., "Drying and Curing Inks and Coatings on Glass" (Mar. 16, 2013) Glass Magazine 5 pages.

Doremus, R.H., "Structure, Properties, and Processing" (2008) In: Ceramic and Glass Materials (Eds: J.F. Shackelford & R.H. Doremus) 33 pages.

Francis, J., "ECG monitoring leads and special leads" (2016) Indian Pacing and Electrophysiology Journal 16:92-95.

Kingery, W.D., "Introduction to Ceramics" (1960) Eds: John Wiley & Sons, Inc. 23 pages.

Loehman, R.E., "Surfaces, Interfaces, Thin Films" (1993) In: Characterization of Ceramics, Materials Characterization Series (Eds: R.E. Loehman, J.E. Fitzpatrick) 13 pages.

Mendelson, Y. et al., "A Wearable Reflectance Pulse Oximeter for Remote Physiological Monitoring" (Aug 30-Sep. 3, 2006) Proceedings of the 28th IEEE, EMBS Annual International Conference New York City 4 pages.

Mendelson, Y., "Wearable Wireless Pulse Oximetry for Physiological Monitoring" (Aug. 4, 2008) Presentation—PPL Workshop 34 pages.

Meziane, N. et al. "Dry Electrodes for Electrocardiography"(2013) Physiol. Meas. 34:R47-R69.

Shi, F., "Progress in Modern Ceramics" (2012) In: Ceramic Materials (Ed: Feng Shi) 6 pages.

GreyB, "Google Watch: Convert your arm into a Keyboard" (2014), retrieved from the Internet: URL: https://greybmusings.wordpress.com/2014/02/28/google-smartwatch/ [retrieved Aug. 28, 2023], 4 pages.

U.S. Appl. No. 17/987,429, filed Nov. 15, 2022, Hatanaka et al.

(56) References Cited

OTHER PUBLICATIONS

U.S. Appl. No. 18/075,212, filed Dec. 5, 2022, Pandya et al.
Chen et al., "Dynamics Analysis and Simulation of the Wearable Power Assistance Robot," *Experiment Science and Technology*, 2009, 5 pages.
Dozza et al., "A Portable Audio-biofeedback System to Improve Postural Control," Proceedings of the 26th Annual International Conference of the IEEE EMBS, San Francisco, CA, Sep. 1-5, 2004, pp. 4799-4802.
Nirjon et al., MusicalHeart: A Hearty Way of Listening to Music, *SenSys* 2012, Nov. 6-9, 2012, Toronto, Ontario, Canada, pp. 1-14.
Ohgi et al., "Stroke phase discrimination in breaststroke swimming using a tri-axial acceleration sensor device," *Sports Engineering*, vol. 6, No. 2, Jun. 1, 2003, pp. 113-123.
Onizuka et al., Head Ballistocardiogram Based on Wireless Multi-Location Sensors, 2015 EEE, pp. 1275-1278.
Zijlstra et al., "Assessment of spatio-temporal gait parameters from trunk accelerations during human walking," *Gait & Posture*, vol. 18, No. 2, Oct. 1, 2003, pp. 1-10.

\* cited by examiner

SENSING HEALTH PARAMETERS IN WEARABLE DEVICES

CROSS-REFERENCE TO RELATED APPLICATION

This application is a nonprovisional of, and claims the benefit under 35 U.S.C. § 119(e) of and priority to U.S. Provisional Patent Application No. 63/239,358, filed Aug. 31, 2021, the contents of which are incorporated herein by reference in their entirety.

TECHNICAL FIELD

The described embodiments relate generally to wearable devices, systems, and methods thereof for determining a health parameter of a user. More particularly, the present embodiments relate to measuring health parameters with more accuracy and reliability using sensors in wearable devices.

BACKGROUND

Sensors are included in many of today's electronic devices, including electronic devices such as phones, smartphones, computers (e.g., tablet computers or laptop computers), wearable electronic devices (e.g., electronic watches, smart watches, or health or fitness monitors), game controllers, navigation systems (e.g., vehicle navigation systems or robot navigation systems), earbuds, headphones, headsets, glasses, and so on. Sensors may variously sense the presence of objects, distances to objects, proximities of objects, movements of objects (e.g., whether objects are moving, or the speed, acceleration, or direction of movement of objects), compositions of objects, a biophysical condition or status of a user (e.g., a user's health or fitness), and so on.

Given the wide range of sensor applications, any new development in the configuration or operation of a sensor can be useful. New developments that may be particularly useful are developments that reduce the cost, size, complexity, part count, or manufacture time of the sensor, or developments that improve the sensitivity, functionality, accuracy, or speed of sensor operation. It is increasingly desirable to have more accurate and reliable measurement sensors in wearable devices, and to have measurement sensors that are lower cost.

SUMMARY

The term embodiment and like terms, e.g., implementation, configuration, aspect, example, and option, are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter. This summary is also not intended to be used in isolation to determine the scope of the claimed subject matter. The subject matter should be understood by reference to appropriate portions of the entire specification of this disclosure, any or all drawings, and each claim.

Embodiments of this disclosure are directed to a wearable device having a housing, a display, and a sensor system. The display may be at least partially surrounded by the housing. The sensor system may be housed at least partially in the housing. The sensor system may include a first sensor, a second sensor, and a controller. The first sensor may be configured to contact a body part of a user and generate a first signal. The second sensor may be configured to sense a mechanical wave in an ambient environment of the wearable device and generate a second signal. The controller may be configured to generate a resultant signal by removing noise from the first signal using the second signal, and determine a health parameter of the user from the resultant signal.

Embodiments of this disclosure are also directed to a wearable device having a housing and a sensor system. The housing may include a main body and at least one stem extending from the main body. The sensor system may be housed at least partially in the housing. The sensor system may include a first sensor, a second sensor, and a controller. The first sensor may be configured to sense an aspect of a body part of a user when the wearable device is worn and generate a first signal. The second sensor may be configured to sense a mechanical wave in an ambient environment of the wearable device and generate a second signal. The controller may be configured to combine the first signal and the second signal, and determine a health parameter of the user using the combined first and second signals.

Embodiments of this disclosure are also directed to a method of determining a health parameter of a user. The method may include receiving a first signal from a first sensor of an electronic device when the first sensor is in contact with a body part of the user. The method may further include receiving a second signal from a second sensor of the electronic device while the second sensor is spaced apart from the body part and sensing a mechanical wave of an ambient environment of the electronic device. The method may further include removing at least a portion of a noise signal from the first signal, using the second signal, to form a resultant signal. The method subsequently includes determining the health parameter of the user from the resultant signal.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims. Additional aspects of the disclosure will be apparent to those of ordinary skill in the art in view of the detailed description of various embodiments, which is made with reference to the drawings, a brief description of which is provided below.

BRIEF DESCRIPTION OF THE SEVERAL VIEWS OF THE DRAWINGS

The disclosure will be readily understood by the following detailed description in conjunction with the accompanying drawings, wherein like reference numerals designate like structural elements, and in which.

Figure 1A:
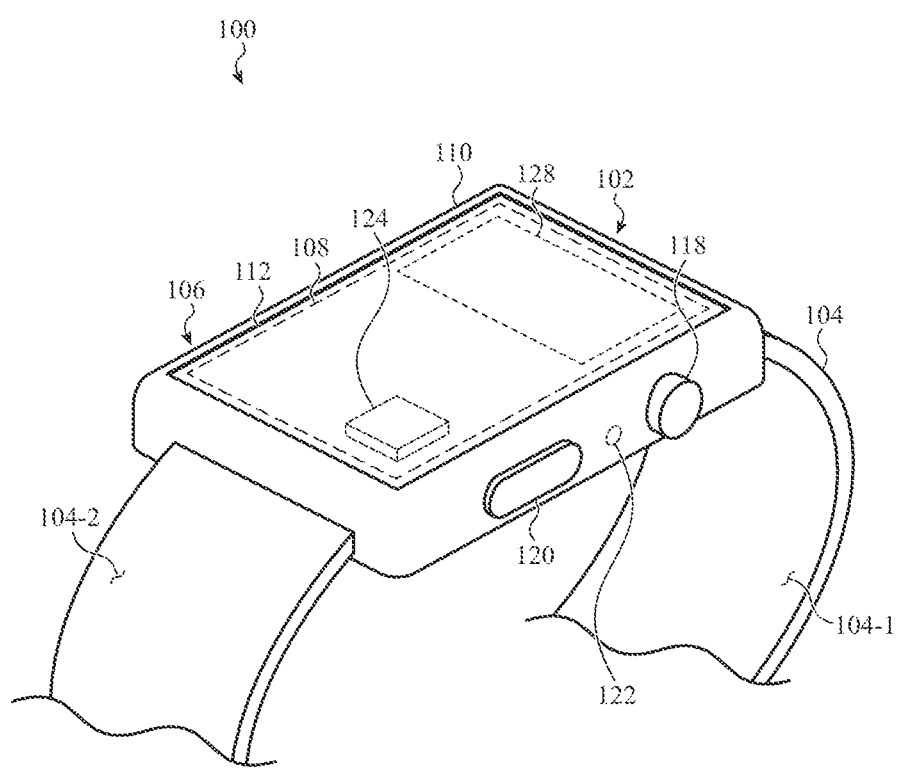
FIG. 1A shows a perspective top view of an example wearable device having sensors for determining a health parameter of the user of the wearable device, according to aspects of the present disclosure.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

The present disclosure is susceptible to various modifications and alternative forms, and some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Various embodiments are described with reference to the attached figures, where like reference numerals are used throughout the figures to designate similar or equivalent elements. The figures are not necessarily drawn to scale and are provided merely to illustrate aspects and features of the present disclosure. Numerous specific details, relationships, and methods are set forth to provide a full understanding of aspects and features of the present disclosure, although one having ordinary skill in the relevant art will recognize that these aspects and features can be practiced without one or more of the specific details, with other relationships, or with other methods. In some instances, well-known structures or operations are not shown in detail for illustrative purposes. The various embodiments disclosed herein are not necessarily limited by the illustrated ordering of acts or events, as some acts may occur in different orders and/or concurrently with other acts or events. Furthermore, not all illustrated acts or events are necessarily required to implement aspects and features of the present disclosure.

For purposes of the present detailed description, unless specifically disclaimed, and where appropriate, the singular includes the plural and vice versa. The word "including" means "including without limitation." Moreover, words of approximation, such as "about," "almost," "substantially," "approximately," and the like, can be used herein to mean "at," "near," "nearly at," "within 3-5% of," "within acceptable manufacturing tolerances of," or any logical combination thereof. Similarly, terms "vertical" or "horizontal" are intended to additionally include "within 3-5% of" a vertical or horizontal orientation, respectively.

Additionally, directional terminology, such as "top", "bottom", "upper", "lower", "front", "back", "over", "under", "above", "below", "left", "right", etc. is used with reference to the orientation of some of the components in some of the figures described below. Because components in various embodiments can be positioned in a number of different orientations, directional terminology is used for purposes of illustration only and is in no way limiting. The directional terminology is intended to be construed broadly, and therefore should not be interpreted to preclude components being oriented in different ways. These words are intended to relate to the equivalent direction as depicted in a reference illustration; as understood contextually from the object(s) or element(s) being referenced, such as from a commonly used position for the object(s) or element(s); or as otherwise described herein. Further, it is noted that the term "signal" means a waveform (e.g., electrical, optical, magnetic, mechanical or electromagnetic) capable of traveling through a medium such as DC, AC, sinusoidal-wave, triangular-wave, square-wave, vibration, and the like.

Also, as used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

Embodiments of the disclosure are directed to wearable devices, systems, and methods of determining a health parameter of a user, using sensors in the wearable devices. In some embodiments, one or more optical sensors positioned on a watch, phone, cuff, earbud, or other device can be used to measure health metrics of a user. For example, heart rate and peripheral oxygen saturation (SpO2) can be measured using infrared (IR), red, and green light-emitting diodes (LEDs). In other embodiments, non-optical sensors, such as piezoelectric or acoustic sensors, can also be used to measure health metrics, and can enable continuous or on-demand health metric measuring or monitoring. Non-optical sensors are interesting because of their potential to reduce power consumption requirements beyond what is possible with optical sensors. This can be advantageous in that consumer products typically face challenges in terms of size, battery life, and so on. Any reduction in a device's power consumption requirements can be beneficial in terms of extending the device's use between battery charges, and/or enabling the device to operate with a battery having a reduced size or weight.

As described herein, two or more piezoelectric polyvinylidene fluoride (PVDF) sensors and/or acoustic sensors may be integrated into a wearable device and used to obtain relevant signals for health sensing. The wearable device may be watches, phones, earbuds, glasses, tablet computers, sleep products (e.g., in-bed sensor mats), cuffs (e.g., blood pressure cuffs), chest straps, and the like. This arrangement works by measuring physiological health parameters and rejecting unrelated external noises that affect the signals associated with the physiological health parameters. This enables external noise interferences to be attenuated, thus improving signal to noise ratio (SNR) and enabling localized micro vibration sensing at low power consumption compared to optical sensors. Health metrics information can be extracted from sensed signals after subtracting out external aggressors (e.g., noise), and in some embodiments, applying filtering to an acquired signal, to determine a user's heart rate (HR), respiration rate, the presence of micro vibrations, and so on. In some embodiments, multiple types of sensors may be included in a device to improve SNR and/or reduce power consumption.

Relevant sensors to improve signal quality include microphones, piezoelectric PVDF sensors, capacitive gap sensors, strain gauges, accelophones, and accelerometers. Such sensors may increase a sensing bandwidth, sensitivity, SNR, or dynamic range or linearity of the measured physiological health parameters. Such sensors may be used to acquire a user's HR, ballistocardiogram (BCG)/seismocardiogram (SCG), respiratory motion, lung sounds, and so on. A user's respiration rate may be measured using seismocardiography. Such sensors can be less susceptible to body perspiration, environmental acoustic noise, motion artifacts, and so on. In some embodiments, such sensors may be a companion to optical sensing and may be switched ON or OFF depending on an optical SNR.

These and other wearable systems, devices, methods, and apparatus are described with reference to FIGS. 1A-6. However, those skilled in the art will readily appreciate that the detailed description given herein with respect to these figures is for explanatory purposes only and should not be construed as limiting.

Figure 1B:
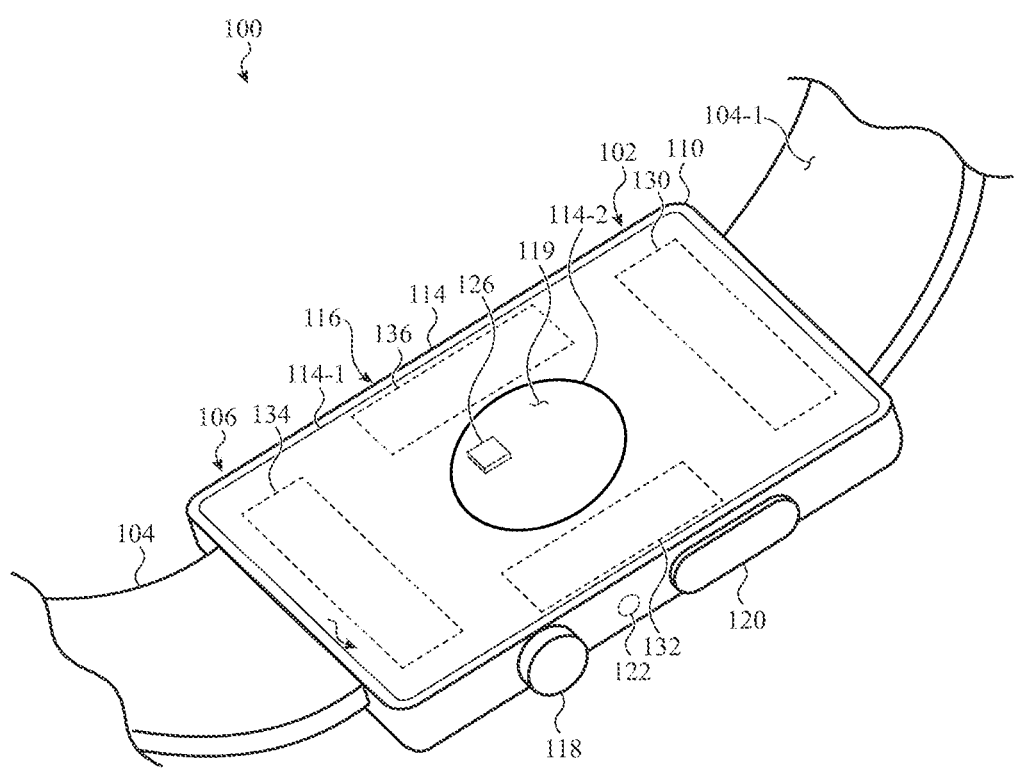
FIG. 1B shows a perspective rear view of the example wearable device of FIG. 1A, according to aspects of the present disclosure.
Figure 1C:
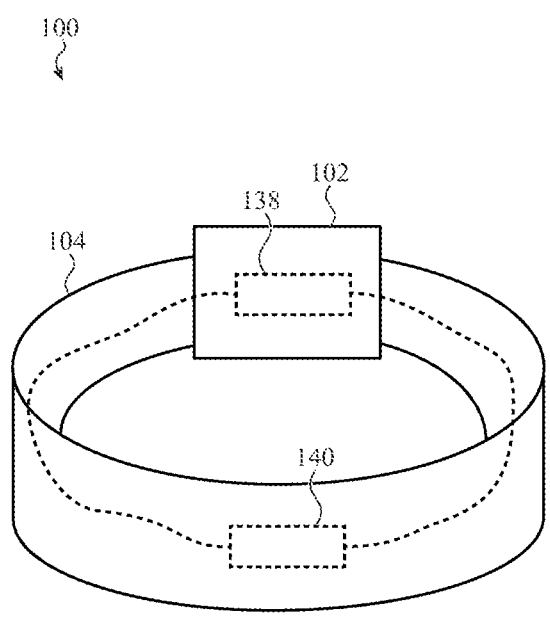
FIG. 1C shows a perspective side view of the example wearable device of FIG. 1A, according to aspects of the present disclosure.

FIGS. 1A-1C show a perspective top view, a perspective rear view, and a perspective side view, respectively, of an example wearable device 100 having sensors for determining a health parameter of the user of the wearable device 100. The wearable device 100 may be a smartwatch, a fitness monitor, a health diagnostic device, or alternatively, any type of wearable and portable device. The wearable device 100 includes a housing 102 including a main body 106, and a band 104 (e.g., wrist band) attached to the housing 102. The band 104 is configured to secure the wearable device 100 to a body part (e.g., an arm, wrist, leg, ankle, or waist) or skin of the user. In different embodiments, coupling mechanisms other than the band 104 may be used to secure the wearable device 100 to at least a portion of a body of the user or a stationary object.

The housing 102 may include an input or selection device, such as a crown 118 or an input button 120. The housing 102 at least partially surrounds a display 108. In some embodiments, the housing 102 may include a sidewall 110, which sidewall 110 may support a front cover 112 (FIG. 1A) and/or a back cover 114 (FIG. 1B). The front cover 112 may be positioned over the display 108, and may provide a window through which the display 108 may be viewed. In some embodiments, the display 108 may be attached to (or abut against) the sidewall 110 and/or the front cover 112. In alternative embodiments of the wearable device 100, the display 108 may not be included and/or the housing 102 may have an alternative configuration.

The display 108 may include one or more light-emitting elements including, for example, light-emitting elements that define a light-emitting diode (LED) display, organic LED (OLED) display, liquid crystal display (LCD), electroluminescent (EL) display, or other type of display. In some embodiments, the display 108 may include, or be associated with, one or more touch and/or force sensors that are configured to detect a touch and/or a force applied to a surface of the front cover 112.

In some embodiments, the sidewall 110 of the housing 102 may be formed using one or more metals (e.g., aluminum or stainless steel), polymers (e.g., plastics), ceramics, or composites (e.g., carbon fiber). The front cover 112 may be formed, for example, using one or more of glass, a crystal (e.g., sapphire), or a transparent polymer (e.g., plastic) that enables a user to view the display 108 through the front cover 112. In some non-limiting embodiments, a portion of the front cover 112, such as a perimeter portion of the front cover 112, may be coated with an opaque ink to obscure components included within the housing 102. In some embodiments, all of the exterior components of the housing 102 may be formed from a transparent material, and components within the device 100 may or may not be obscured by an opaque ink or opaque structure within the housing 102.

The back cover 114 may be formed using the same material(s) that are used to form the sidewall 110 or the front cover 112. In some embodiments, the back cover 114 may be part of a monolithic element that also forms the sidewall 110. In other embodiments, and as shown, the back cover 114 may be a multi-part back cover, such as a back cover 114 having a first back cover portion 114-1 attached to the sidewall 110 and a second back cover portion 114-2 attached to the first back cover portion 114-1. The second back cover portion 114-2 may, in some embodiments, have a circular perimeter and an exterior surface 119 having an arcuate profile.

The front cover 112, back cover 114, or first back cover portion 114-1 may be mounted to the sidewall 110 using fasteners, adhesives, seals, gaskets, or other components. The second back cover portion 114-2, when present, may be mounted to the first back cover portion 114-1 using fasteners, adhesives, seals, gaskets, or other components.

A display stack or device stack (hereafter referred to as a "stack") including the display 108 may be attached to (or abutted against) an interior surface of the front cover 112 and extend into an interior volume of the wearable device 100. In some embodiments, the stack may include a touch sensor (e.g., a grid of capacitive, resistive, strain-based, ultrasonic, or other type of touch sensing elements), or other layers of optical, mechanical, electrical, or other types of components.

In some embodiments, the touch sensor (or part of a touch sensor system) may be configured to detect a touch applied to an outer surface of the front cover 112, such as a display surface of the wearable device 100.

In some embodiments, a force sensor (or part of a force sensor system) may be positioned within the interior volume below and/or to the side of the display 108 (and in some embodiments, within the device stack). The force sensor (or force sensor system) may be triggered in response to the touch sensor detecting one or more touches on the front cover 112, or a location or locations of one or more touches on the front cover 112, and may determine an amount of force associated with each touch, or an amount of force associated with the collection of touches as a whole. The force sensor (or force sensor system) may alternatively trigger operation of the touch sensor (or touch sensor system), or may be used independently of the touch sensor (or touch sensor system).

The wearable device 100 includes a sensor system 116 that is at least partially housed in the housing 102. The various sensors in the sensor system 116 are capable of acquiring physiological information from the wearer or user of the wearable device 100 (e.g., a heart rate, respiration rate, blood oxygenation level, a ballistocardiogram, a seismocardiogram, blood pressure level, a blood flow rate, a blood glucose level, a partial thromboplastin time, body temperature, etc.), or to determine a status of the wearable device 100 (e.g., whether the wearable device 100 is being worn or a tightness of the wearable device 100). The different sensors in the sensor system 116 may include a piezoelectric PVDF sensor, a strain sensor, a piezoelectric sensor, a capacitive gap sensor, an acoustic sensor, a microphone, an accelophone, an image sensor, a heat sensor, a motion sensor, a proximity sensor, an accelerometer, a gyroscope, or a pressure transducer.

In some non-limiting embodiments, one or more such sensors may include a number of electromagnetic radiation emitters, such as visible light and/or infrared (IR) emitters, and/or a number of electromagnetic radiation detectors, such as visible light and/or IR detectors, such as electromagnetic radiation detectors including any of the detector pixels described herein.

In some embodiments, the wearable device 100 may have a port 122 (or set of ports) on a side of the housing 102 (or elsewhere), and an ambient pressure sensor, ambient temperature sensor, internal/external differential pressure sensor, gas sensor, particulate matter concentration sensor, or air quality sensor may be positioned in or near the port(s) 122. Further, in some embodiments, the wearable device 100 may include an image sensor configured for biometric authentication of the user.

The sensor system 116 in the wearable device 100 includes a first sensor 126 disposed on or attached to the back cover 114, or alternatively, on an interior surface 104-1 of the band 104 so that the first sensor 126 is in contact of a body part or skin of the user. In non-limiting embodiments, the first sensor 126 is configured to detect a change in vibration, motion, or radiation associated with a physiological measurement of the user and generate a first signal based on the physiological measurement. In some embodiments, the first sensor 126 is a piezoelectric PVDF sensor or strain sensor. The first sensor 126 may alternatively be an optical sensor or other type of sensor. The first sensor 126 may emit or transmit signals through the housing 102 (or back cover 114) and/or receive signals or sense conditions through the housing 102 (or back cover 114).

Additionally, a second sensor 128 is disposed on or attached to the front cover 112 of the housing 102, or alternatively, on an exterior surface 104-2 of the band 104. The second sensor 128 is configured to sense a mechanical wave in an ambient environment of the wearable device 100 and generate a second signal. In some embodiments, the second sensor 128 is embedded somewhere in the band 104 to be used as a reference to measure and reject external noise aggressors. In various embodiments, the second sensor 128 may be a piezoelectric PVDF sensor, a strain sensor, a capacitive gap sensor, an acoustic sensor, a microphone, an accelophone, and the like. In some embodiments, the second sensor 128 is embedded on the display 108 for self-examination and acquisition of other stethoscope sounds. In other embodiments, the second sensor 128 may be located at a remote location from the wearable device 100, such as on a chest trap, on blood pressure cuffs, or on an in-bed sensor mat.

Additionally or alternatively, the sensor system 116 in the wearable device 100 may include multi-pixel PVDF, strain, or capacitive gap sensors 130, 132, 134, and 136 embedded in or around the back cover 114 (e.g., around the second back cover portion 114-2) to measure alternating current (AC) lung and heart signals. This arrangement can be used to measure partial thromboplastin time (PTT), respiration rate (RR), or heart rate (HR), by measuring and rejecting external noises through the multi-location sensor arrangement. This multi-pixel arrangement can also be used to detect whether the wearable device 100 is being worn and/or a tightness of the wearable device 100 while worn, or to detect a quality of contact between the skin of the user and the wearable device 100, or to detect any rotation, skew, or an orientation of the wearable device 100. For example, whether the wearable device 100 is being worn, or the quality of contact with a user's skin, can be determined based at least partly based on the strengths of signals generated by the sensors 130, 132, 134, 136 and, in some cases, the amount of noise in the signals. As another example, whether the wearable device 100 is skewed with respect to a user's skin (e.g., not resting flat on the user's skin) can be determined at least partly based on comparisons of, and differences in, the signals generated by the sensors 130, 132, 134, 136. These detections of device condition(s) and orientation can be useful in conjunction with measurement of biometric signals (e.g., heart rate, respiration rate, BCG, etc.) and physiological signals because they can help identify issues with signal quality. For example, when measuring SpO2, detecting tightness of the wearable device 100, or a quality of contact of the wearable device 100 with the user's skin is needed to accurately measure a perfusion index.

Additionally or alternatively, the wearable device 100 may include a multi-pixel sensor arrangement including sensors 138, 140 embedded into the back cover 114 and the band 104 (or, additionally or alternatively, two or more such sensors embedded in the band 104).

Additionally or alternatively, the sensor system 116 may include a temperature sensor (not shown) embedded on the back cover 114 for measuring a temperature of the wrist skin, and a temperature sensor (not shown) embedded on the front cover 112 for measuring an ambient temperature. The measured ambient temperature and the measured skin temperature may then be used to calculate a body temperature of the user (e.g., by adjusting a temperature acquired by the back cover temperature sensor in response to an ambient temperature measured by the front cover temperature sensor).

The wearable device 100 may include a controller 124 (e.g., a processor and/or other components) configured to determine or extract, at least partly in response to signals received directly or indirectly from the sensors 126, 128, physiological health parameters of the user and/or a status of the wearable device 100, as mentioned above. As a non-limiting example, the controller 124 may receive a first signal from the first sensor 126 comprising physiological information (e.g., heart rate, respiration rate, etc.) detected through contact of the user's skin. At the same time, the controller 124 may receive a second signal from the second sensor 128, where the second signal includes external noise aggressors in the ambient environment of the wearable device 100. The controller 124 uses the second signal to generate a resultant signal by removing noise captured by the first signal. In some embodiments, this is accomplished by simply subtracting the second signal from the first signal. In some embodiments, the controller 124 may further apply filters to the resultant signal to extract the health parameters or statuses.

In some embodiments, the controller 124 may be configured to convey the determined or extracted health parameters or statuses via an output device of the wearable device 100. For example, the controller 124 may cause the indication(s) to be displayed on the display 108, indicated via audio or haptic outputs, transmitted via a wireless communications interface or other communications interface, and so on. The controller 124 may also or alternatively maintain or alter one or more settings, functions, or aspects of the wearable device 100, including, in some embodiments, what is displayed on the display 108.

Figure 2:
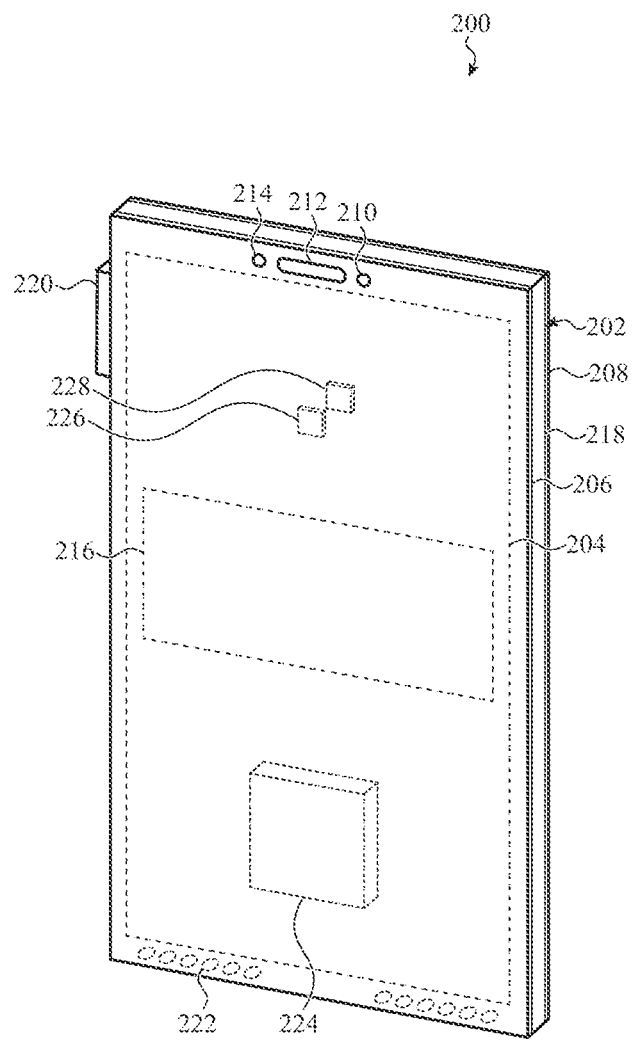
FIG. 2 shows a perspective front view of another example wearable device having sensors for determining a health parameter of the user of the wearable device, according to aspects of the present disclosure.

FIG. 2 shows a perspective front view of an example wearable device 200 having sensors for determining a health parameter of the user of the wearable device 200. The wearable device 200 may be a smartphone, a mobile device, a tablet computer, a portable electronic device, a portable computer, a portable music player, a portable terminal, a vehicle navigation system, a robot navigation system, or other portable or mobile device. The wearable device 200 could also be a device that is semi-permanently located (or installed) at a single location (e.g., a door lock, thermostat, refrigerator, or other appliance).

The wearable device 200 includes a housing 202 that at least partially surrounds a display 204. The housing 202 may include or support a front cover 206 and/or a rear cover 208. The front cover 206 may be positioned over the display 204, and may provide a window through which the display 204 (including images displayed thereon) may be viewed by a user. In some embodiments, the display 204 may be attached to (or abut against) the housing 202 and/or the front cover 206.

The display 204 may include one or more light-emitting elements or pixels, and in some embodiments, may be an LED display, an OLED display, an LCD, an EL display, a laser projector, or another type of electronic display. In some embodiments, the display 204 may include, or be associated with, one or more touch and/or force sensors that are configured to detect a touch and/or a force applied to a surface of the front cover 206.

The various components of the housing 202 may be formed from the same or different materials. For example, a sidewall 218 of the housing 202 may be formed using one or more metals (e.g., stainless steel), polymers (e.g., plastics), ceramics, or composites (e.g., carbon fiber). In some embodiments, the sidewall 218 may be a multi-segment sidewall including a set of antennas. The antennas may form structural components of the sidewall 218. The antennas may be structurally coupled (to one another or to other components) and electrically isolated (from each other or from other components) by one or more non-conductive segments of the sidewall 218. The front cover 206 may be formed, for example, using one or more of glass, a crystal (e.g., sapphire), or a transparent polymer (e.g., plastic) that enables a user to view the display 204 through the front cover 206. In some embodiments, a portion of the front cover 206 (e.g., a perimeter portion of the front cover 206) may be coated with an opaque ink to obscure components included within the housing 202. The rear cover 208 may be formed using the same material(s) that are used to form the sidewall 218 or the front cover 206, or may be formed using a different material or materials. In some embodiments, the rear cover 208 may be part of a monolithic element that also forms the sidewall 218 (or in some embodiments, where the sidewall 218 is a multi-segment sidewall, those portions of the sidewall 218 that are non-conductive). In still other embodiments, all of the exterior components of the housing 202 may be formed from a transparent material, and components within the wearable device 200 may or may not be obscured by an opaque ink or opaque structure within the housing 202.

The front cover 206 may be mounted to the sidewall 218 to cover an opening defined by the sidewall 218 (i.e., an opening into an interior volume in which various electronic components of the wearable device 200, including the display 204, may be positioned). The front cover 206 may be mounted to the sidewall 218 using fasteners, adhesives, seals, gaskets, or other components.

A display stack or device stack (hereafter referred to as a "stack") including the display 204 (and in some embodiments, the front cover 206) may be attached to (or abutted against) an interior surface of the front cover 206 and extend into the interior volume of the wearable device 200. In some embodiments, the stack may also include a touch sensor (e.g., a grid of capacitive, resistive, strain-based, ultrasonic, or other type of touch sensing elements), or other layers of optical, mechanical, electrical, or other types of components. In some embodiments, the touch sensor (or part of a touch sensor system) may be configured to detect a touch applied to an outer surface of the front cover 206 (e.g., to a display surface of the wearable device 200).

In some embodiments, a force sensor (or part of a force sensor system) may be positioned within the interior volume below and/or to the side of the display 204 (and in some embodiments, within the stack). The force sensor (or force sensor system) may be triggered in response to the touch sensor detecting one or more touches on the front cover 206 (or indicating a location or locations of one or more touches on the front cover 206), and may determine an amount of force associated with each touch, or an amount of force associated with the collection of touches as a whole.

The wearable device 200 includes a sensor system 216 that is at least partially housed within the housing 202. The various sensors in the sensor system 216 are capable of acquiring physiological information from the wearer or user of the wearable device 200 (e.g., a heart rate, a respiration rate, a blood oxygenation level, a ballistocardiogram, a seismocardiogram, a blood pressure level, a blood flow rate, a blood glucose level, a partial thromboplastin time, etc.), or to determine a status of the wearable device 200 (e.g., whether the wearable device 200 is being worn or a tightness of the wearable device 200). The different sensors in the sensor system 216 may include a piezoelectric PVDF sensor, a strain sensor, a piezoelectric sensor, a capacitive gap sensor, an acoustic sensor, a microphone, an accelophone, an image sensor, a heat sensor, a motion sensor, a proximity sensor, an accelerometer, a gyroscope, or a pressure transducer.

In some embodiments, one or more such sensors may include a number of electromagnetic radiation emitters (e.g., visible light and/or IR emitters) and/or a number of electromagnetic radiation detectors (e.g., visible light and/or IR detectors, such as electromagnetic radiation detectors including any of the detector pixels described herein). In some embodiments, the wearable device 200 may have an ambient pressure sensor, an ambient temperature sensor, an internal/external differential pressure sensor, a gas sensor, a particulate matter concentration sensor, or an air quality sensor positioned at one or more locations on the housing 202. Further, in some embodiments, the wearable device 200 may include an image sensor configured for biometric authentication of the user.

In some embodiments, the wearable device 200 may include a first sensor 226 integrated into or with the display 204, for purposes of monitoring a user's health. In some embodiments, the first sensor 226 may be capable of sensing physiological information from a body part or skin of a user of the wearable device 200. In non-limiting embodiments, the first sensor 226 is configured to detect a change in vibration, motion, or radiation associated with a physiological measurement of the user and generate a first signal based on the physiological measurement. In some embodiments, the first sensor 226 may be a PVDF sensor or a strain sensor. The first sensor 226 may emit or transmit signals through the housing 202 and/or receive signals or sense conditions through the housing 202.

Additionally, a second sensor 228 is disposed on or attached to the rear cover 208 of the housing 202. The second sensor 228 is configured to sense a mechanical wave in an ambient environment of the wearable device 200 and generate a second signal. In some embodiments, the second sensor 228 may be used as a reference to measure and reject external noise aggressors. In various embodiments, the second sensor 228 may be a PVDF sensor, a strain sensor, a piezoelectric sensor, a capacitive gap sensor, an acoustic sensor, a microphone, an accelophone, and the like. In some embodiments, the second sensor 228 is embedded on the display 108 for self-examination and acquisition of other stethoscope sounds. In other embodiments, the second sensor 228 may be located at a remote location from the wearable device 200, such as on a chest trap, on blood pressure cuffs, or on an in-bed sensor mat.

The wearable device 200 may include a controller 224 (e.g., a processor and/or other components) configured to determine or extract, at least partly in response to signals received directly or indirectly from the sensors 226, 228, physiological health parameters of the user, a status of the wearable device 200, or parameters of an environment of the wearable device 200 (e.g., air quality), or a composition of a target or object, as mentioned above. As a non-limiting example, the controller 224 may receive a first signal from the first sensor 226 comprising physiological information (e.g., heart rate, respiration rate, etc.) detected through contact of the user's skin. At the same time, the controller 224 may receive a second signal from the second sensor 228, where the second signal includes external noise aggressors in the ambient environment of the wearable device 200. The controller 224 uses the second signal to generate a resultant signal by removing noise captured by the first signal. In some embodiments, this is accomplished by simply subtracting the second signal from the first signal. In some embodiments, the controller 224 may further apply filters to the resultant signal to extract the health parameters or statuses.

In some embodiments, the controller 224 may be configured to convey the determined or extracted health parameters or statuses via an output device of the wearable device 200. For example, the controller 224 may cause the indication(s) to be displayed on the display 204, indicated via audio or haptic outputs, transmitted via a wireless communications interface or other communications interface, and so on. The controller 224 may also alternatively maintain or alter one or more settings, functions, or aspects of the wearable device 200, including, in some embodiments, what is displayed on the display 204.

The wearable device 200 may include various other components. For example, the front of the wearable device 200 may include one or more front-facing cameras 210 (including one or more image sensors), speakers 212, microphones 214 or other audio components (e.g., audio, imaging, and/or sensing components) that are configured to transmit or receive signals to/from the wearable device 200. In some embodiments, a front-facing camera 210, alone or in combination with other sensors, may be configured to operate as a bio-authentication or facial recognition sensor. Additionally or alternatively, the sensor system 216 may be configured to operate as a front-facing camera 210, a bio-authentication sensor, or a facial recognition sensor.

The wearable device 200 may also include input buttons or other input devices positioned along the sidewall 218 and/or on a rear surface of the wearable device 200. For example, a volume button or multipurpose button 220 may be positioned along the sidewall 218, and in some embodiments, may extend through an aperture in the sidewall 218. The sidewall 218 may include one or more ports 222 that allow air, but not liquids, to flow into and out of the wearable device 200. In some embodiments, one or more sensors may be positioned in or near the port(s) 222. For example, an ambient pressure sensor, ambient temperature sensor, internal/external differential pressure sensor, gas sensor, particulate matter concentration sensor, or air quality sensor may be positioned in or near a port 222.

Figure 3:
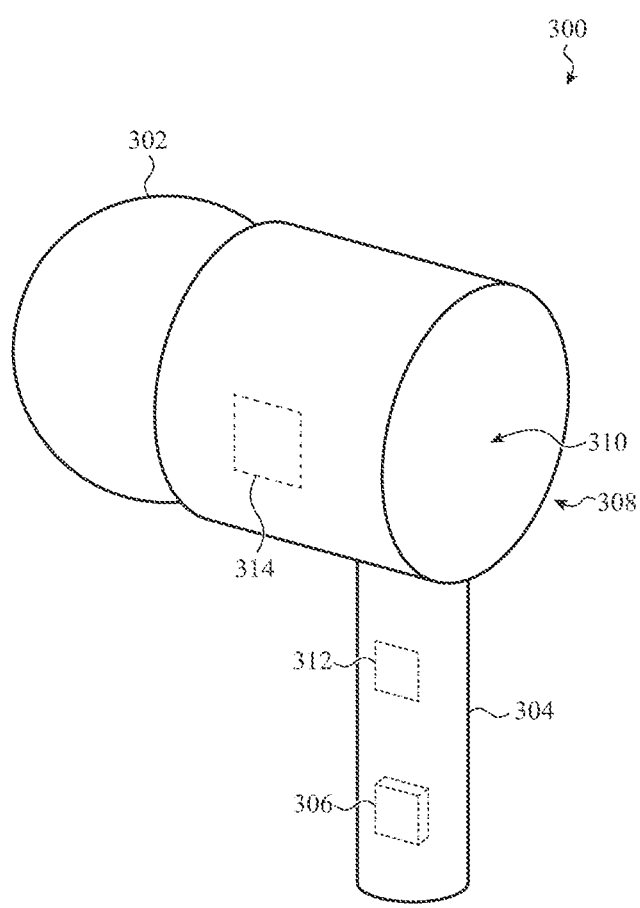
FIG. 3 shows a perspective front view of an example earbud having sensors for determining a health parameter of the user of the earbud, according to aspects of the present disclosure.

FIG. 3 shows a perspective front view of another example wearable device 300 having sensors for determining a health parameter of the user of the wearable device 300. The wearable device 300 may be an earbud, an earphone, and the like. In the embodiment shown in FIG. 3, the wearable device 300 may include a housing 308 (i.e., an earbud housing) having a main body 310, and a stem 304 extending from the main body 310. In other embodiments (not shown), the wearable device 300 may have two parts, each of which is insertable in a user's ear and includes a housing with a main body and a stem. The housing 308 may hold a speaker 302 that can be inserted into a user's ear, an optional microphone 312, and controller 306 that can be used to acquire audio from the microphone 312, transmit audio to the speaker 302, and communicate audio between the speaker 302, the microphone 312, and one or more remote devices. The controller 306 may communicate with a remote device wirelessly (e.g., via a wireless communications interface, using a Wi-Fi, BLUETOOTH®, or cellular radio communications protocol, for example) or via one or more wires (e.g., via a wired communications interface, such as a Universal Serial Bus (USB) communications interface). In addition to communicating audio, the controller 306 may transmit or receive instructions and so on.

In some embodiments, the wearable device 300 may include one or more sensors 314 (e.g., PVDF sensor or strain sensor) integrated into the housing 308 for opportunistic/passive health monitoring. In non-limiting embodiments, the sensors 314 are configured to detect a change in vibration, motion, or radiation associated with a physiological measurement of the user and generate a first signal based on the physiological measurement. In some embodiments, a first one of the sensors 314 may be disposed on the main body 310, while a second one of the sensors 314 may be disposed on the stem 304. In other embodiments, all of the sensors 314 may be either located on the stem 304 or on the main body 310.

The controller 306 may include a processor and/or other components that are configured to determine or extract, at least partly in response to signals received directly or indirectly from the speaker 302, the microphone 312, the one or more of the sensors 314, information related to a proximity of a user, an input of a user, and so on. As a non-limiting example, the controller 306 may receive a first signal from one of the sensors 314 comprising physiological health parameters detected through contact of the user's skin, as described above. At the same time, the controller 306 may receive a second signal from the microphone 312, where the second signal includes external noise aggressors in the ambient environment of the wearable device 300. The controller 306 may use the second signal to generate a resultant signal by removing noise captured by the first signal. In some embodiments, this may be accomplished by simply subtracting the second signal from the first signal. In some embodiments, the controller 306 may further apply filters to the resultant signal to extract the health parameters. In some embodiments, the first signal may be received from a PVDF sensor, strain sensor, acoustic sensor, or temperature sensor 314 on the main body 310 and in contact with a user's skin, and the second signal may be received from a PVDF sensor, strain sensor, acoustic sensor, or temperature sensor 314 on the stem 304 and in contact with an ambient environment of a user's ear.

In some embodiments, a user may wear a pair of the wearable devices 300, in the form of separate earbuds, or different earphone housings of a headset, and so on. In these embodiments, environmental and/or physiological signals specific to each side of a user's head (e.g., each year) can be measured. In such embodiments, an accurate and precise clock/crystal embedded within each wearable device 300 or housing 308 can be used to synchronize and align time-stamped and/or time series measurements obtained from the sensors 314 of different wearable devices or housings. As an example, this can enable measurement of wind direction by detecting the relative magnitude of the received signals from sensors 314 positioned on different wearable devices 300 or housings 308 on a user's ears (e.g., PVDF sensors embedded on or inside the housing 308 on each of a user's ears or on each side of the user's head). For example, timings of changes in the signals produced by the sensors 314 can indicate air movement (e.g., pressure changes or acoustic propagation). As another example, this can enable measurement of temperature between the two ears by measuring the heat flux between the two ears using temperature sensors (e.g., sensors 314) in contact with the user (e.g., flexible thermopile sensors embedded inside or on the surface of the housing 308 on each of a user's ears or on each side of the user's head), and extrapolation of the core body temperature of the user.

In some embodiments, the controller 306 may be configured to convey the determined or extracted health parameters or statuses via an output device of the wearable device 300. For example, the controller 306 may cause the indication(s) to be output via the speaker 302 or a haptic device, transmitted via a wireless communications interface or other communications interface, and so on. The controller 306 may also or alternatively maintain or alter one or more settings, functions, or aspects of the wearable device 300, including, in some embodiments, what is output via the speaker 302.

Figure 4:
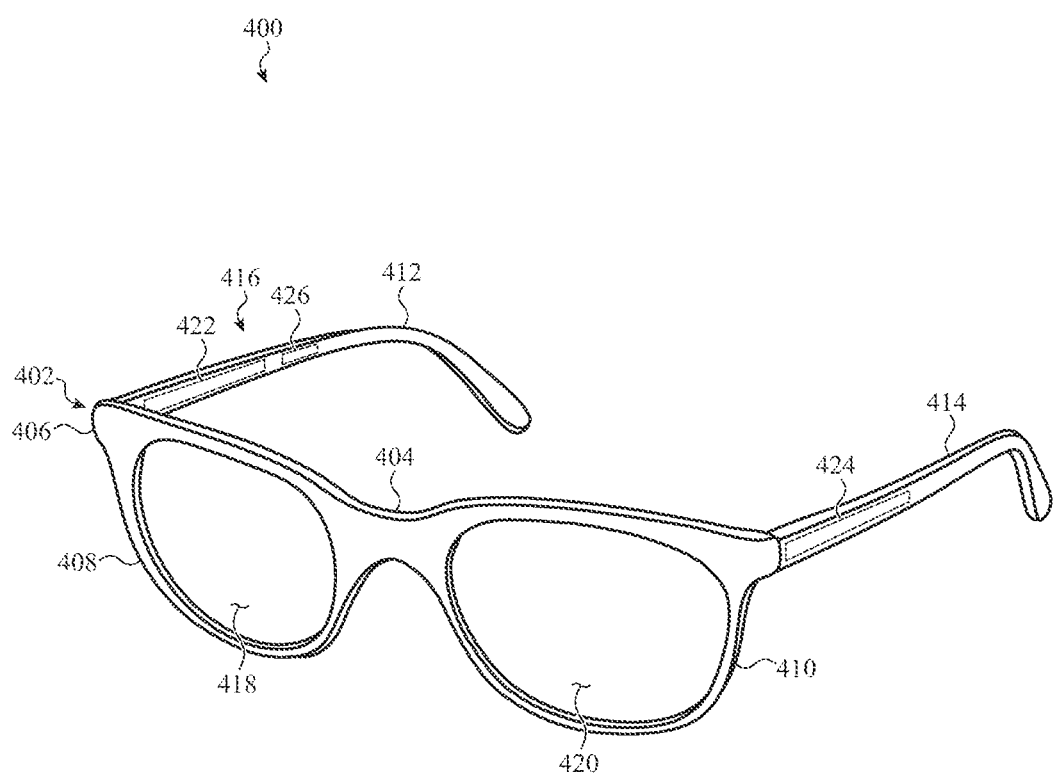
FIG. 4 shows a perspective front view of an example pair of glasses having sensors for determining a health parameter of the user of the pair of glasses, according to aspects of the present disclosure.

FIG. 4 shows a perspective front view of yet another example wearable device 400 having sensors for determining a health parameter of the user of the wearable device 400. The wearable device 400 may be a pair of glasses, smartglasses, and the like. By way of example, the wearable device 400 is shown to include a housing 402 and lenses 418, 420. The housing 402 includes a frame or main body 406 formed by a first lens rim 408, a second lens rim 410, and a bridge 404 connecting the first lens rim 408 to the second lens rim 410. Both a first stem 412 connected to the first lens rim 408 and a second stem 414 connected to the second lens rim 410 extend from the main body 406.

Each of the first lens rim 408 and the second lens rim 410 may hold a respective lens, such as the first lens 418 or the second lens 420. The lenses 418, 420 may or may not magnify, focus, or otherwise alter light passing through the lenses 418, 420. For example, the lenses 418, 420 may correct a user's vision, block bright or harmful light, or simply provide a physical barrier through which light can pass with no or minimal adjustment. In some embodiments, the first and second lenses 418, 420 may be formed of glass or plastic.

In some embodiments, a multi-pixel sensor system 416 may include a first sensor 422 and a second sensor 424 mounted to the wearable device 400. The first sensor 422 and the second sensor 424 may be respectively mounted to the stems 412, 414 or to other components of the wearable device 400. In non-limiting embodiments, the first sensor 422 is configured to detect a change in vibration, motion, or radiation associated with a physiological measurement of the user and generate a first signal based on the physiological measurement. In non-limiting embodiments, the second sensor 424 is configured to sense a mechanical wave in an ambient environment of the wearable device 400 and generate a second signal that may be used as a reference to measure and reject external noise aggressors. The first sensor 422 and the second sensor 424 may, in some embodiments, be connected to a controller 426 that monitors a user's activity or health.

The controller 426 may include a processor and/or other components that are configured to determine or extract, at least partly in response to signals received directly or indirectly from the first sensor 422 and the second sensor 424, information related to a proximity of a user, an input of a user, and so on. As a non-limiting example, the controller 426 may receive a first signal from the first sensor 422 comprising physiological health parameters detected through contact of the user's skin, as described above. At the same time, the controller 426 may receive a second signal from the second sensor 424, where the second signal includes external noise aggressors in the ambient environment of the wearable device 400. The controller 426 uses the second signal to generate a resultant signal by removing noise captured by the first signal. In some embodiments, this is accomplished by simply subtracting the second signal from the first signal. In some embodiments, the controller 426 may further apply filters to the resultant signal to extract the health parameters.

In some embodiments, the controller 426 may be configured to convey the determined or extracted health parameters or statuses via an output device of the wearable device 400. For example, the controller 426 may cause the indication(s) to be output via a remote device or a haptic device, transmitted via a wireless communications interface or other communications interface, and so on.

Figure 5:
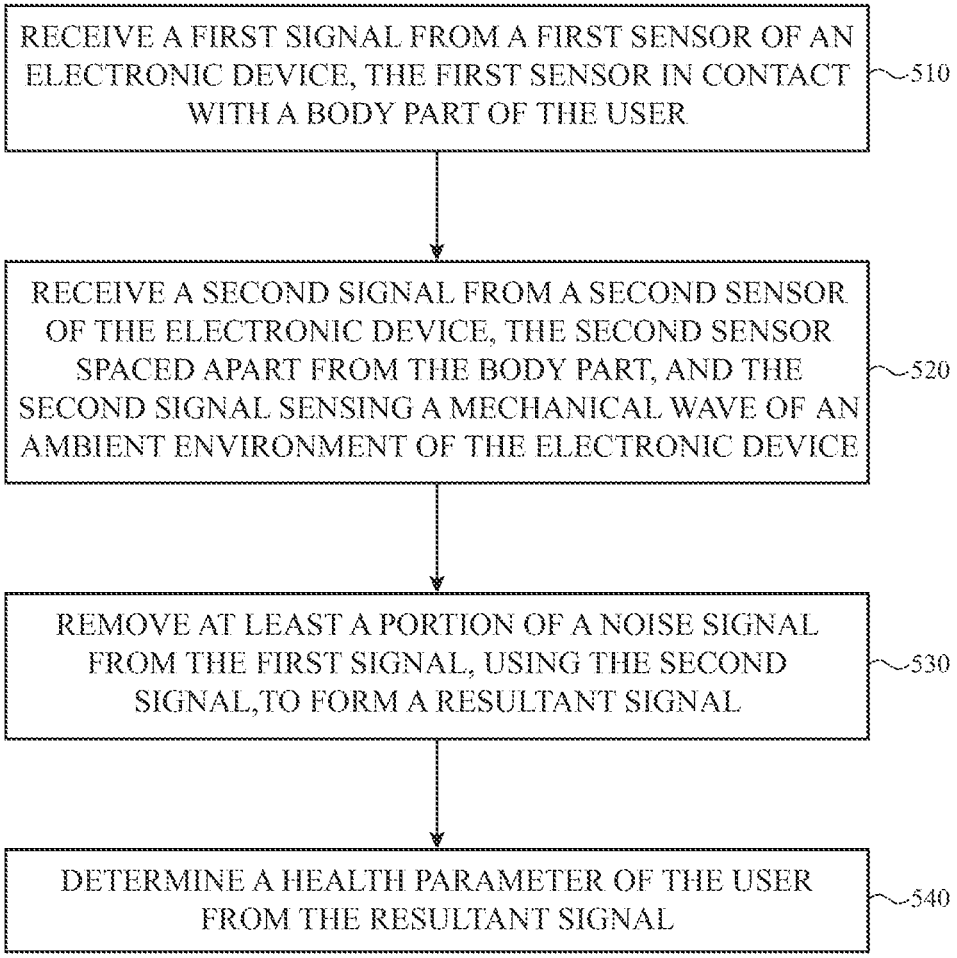
FIG. 5 shows a block diagram of a method of determining a health parameter of a user using the wearable devices of FIGS. 1-4, according to aspects of the present disclosure.

FIG. 5 shows a block diagram 500 of a method of determining a health parameter of a user using the wearable devices 100, 200, 300, and 400 of FIGS. 1A-4. The method starts at block 510, where a first signal from a first sensor of an electronic device is received. The first sensor may be positioned in contact with a body part or a portion of a skin of the user. In some embodiments, the first sensor is configured to detect a change in vibration, motion, or radiation associated with a physiological measurement of the user and generate the first signal based on the physiological measurement. In some embodiments, the first sensor may be a polyvinylidene fluoride (PVDF) sensor, as described above.

In the next step, in block 520, a second signal from a second sensor of the electronic device is received. The second sensor is spaced apart from the body part of the user and configured to sense a mechanical wave of an ambient environment of the electronic device. In some embodiments, the second sensor may be a polyvinylidene fluoride (PVDF) sensor, as described above. In some embodiments, the second signal may be generated at the second sensor in response to receiving a mechanical wave through the ambient environment of the electronic device. This second signal may be used as a reference to measure and reject external noise aggressors.

In block 530, at least a portion of a noise signal from the first signal from the first sensor is removed, using the second signal from the second sensor, to form a resultant signal. In some embodiments, removing at least the portion of the noise signal from the first signal may include subtracting the second signal from the first signal. In some embodiments, the controller 426 may further apply filters to the resultant signal to extract the health parameters.

Finally, in block 540, a health parameter of the user is determined from the resultant signal. In some embodiments, the health parameter of the user is indicative of a health condition of the user such as a heart rate, a respiration rate, a blood oxygenation level, a ballistocardiogram, a seismocardiogram, a blood pressure level, a blood flow rate, a blood glucose level, a partial thromboplastin time, and the like. In some embodiments, the health parameters may be subsequently outputted through a display, an audio output, a haptic output, a wirelessly transmitted message, and the like.

Figure 6:
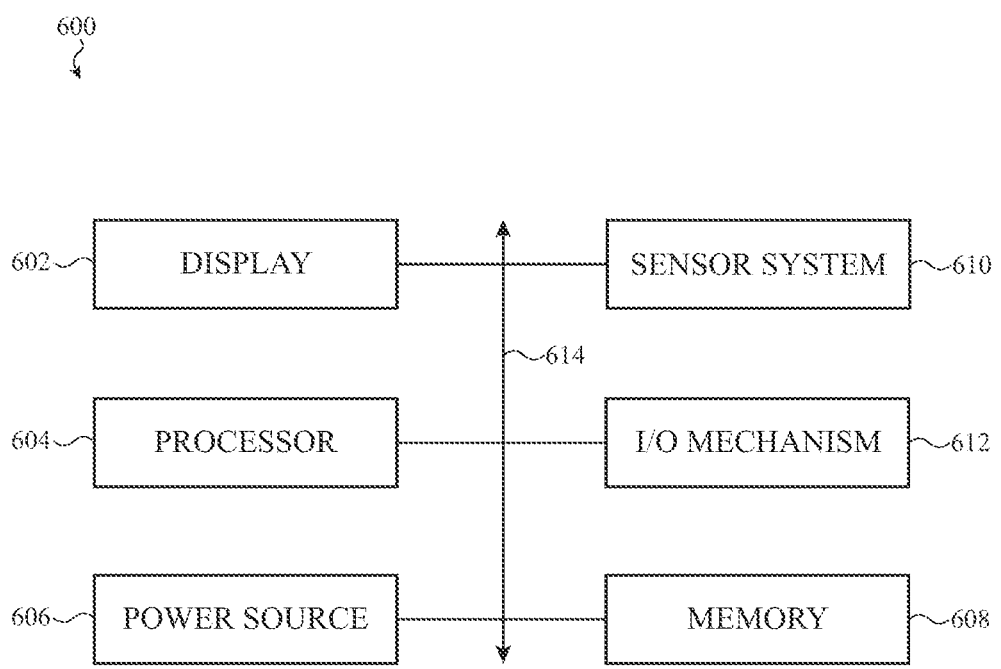
FIG. 6 shows an example schematic representation of an electronic system in the wearable devices of FIGS. 1-4, according to aspects of the present disclosure.

FIG. 6 shows an example schematic representation of an electronic device 600 that is substantially similar to the wearable devices 100, 200, 300, and 400 of FIGS. 1A-4. The electronic device 600 may include an optional electronic display 602 (e.g., a light-emitting display), a processor 604, a power source 606, a memory 608 or storage device, a sensor system 610, or an input/output (I/O) mechanism 612 (e.g., an input/output device, input/output port, or haptic input/output interface). The processor 604 may control some or all of the operations of the electronic device 600. The processor 604 may communicate, either directly or indirectly, with some or all of the other components of the electronic device 600. For example, a system bus or other communication mechanism 614 can provide communication between the electronic display 602, the processor 604, the power source 606, the memory 608, the sensor system 610, and the I/O mechanism 612.

The processor 604 may be implemented as any electronic device capable of processing, receiving, or transmitting data or instructions, whether such data or instructions is in the form of software or firmware or otherwise encoded. For example, the processor 604 may include a microprocessor, a central processing unit (CPU), an application-specific integrated circuit (ASIC), a digital signal processor (DSP), a controller, or a combination of such devices. As described herein, the term "processor" is meant to encompass a single processor or processing unit, multiple processors, multiple processing units, or other suitably configured computing element or elements. In some embodiments, the processor 604 may provide part or all of the controllers described with reference to FIGS. 1A-4.

It should be noted that the components of the electronic device 600 can be controlled by multiple processors. For example, select components of the electronic device 600 (e.g., the sensor system 610) may be controlled by a first processor and other components of the electronic device 600 (e.g., the electronic display 602) may be controlled by a second processor, where the first and second processors may or may not be in communication with each other.

The power source 606 can be implemented with any device capable of providing energy to the electronic device 600. For example, the power source 606 may include one or more batteries or rechargeable batteries. Additionally or alternatively, the power source 606 may include a power connector or power cord that connects the electronic device 600 to another power source, such as a wall outlet.

The memory 608 may store electronic data that can be used by the electronic device 600. For example, the memory 608 may store electrical data or content such as, for example, audio and video files, documents and applications, device settings and user preferences, timing signals, control signals, and data structures or databases. The memory 608 may include any type of memory. By way of example only, the memory 608 may include random access memory, read-only memory, Flash memory, removable memory, other types of storage elements, or combinations of such memory types.

The electronic device 600 includes the sensor system 610, including sensors positioned almost anywhere on the electronic device 600. In some embodiments, the sensor system 610 may include one or more electromagnetic radiation emitters and/or detectors, positioned and/or configured as described with reference to any of FIGS. 1A-4. The sensor system 610 may be configured to sense one or more types of parameters, such as but not limited to, vibration; light; touch; force; heat; movement; relative motion; biometric data (e.g., physiological parameters) of a user; air quality; proximity; position; connectedness; matter type; and so on. By way of example, the sensor system 610 may include one or more of (or multiple of) a heat sensor, a position sensor, a proximity sensor, a light or optical sensor (e.g., an electromagnetic radiation emitter and/or detector), an accelerometer, a pressure transducer, a gyroscope, a magnetometer, a health monitoring sensor, an air quality sensor, and so on. Additionally, the sensor system 610 may utilize any suitable sensing technology, including, but not limited to, interferometric, magnetic, pressure, capacitive, ultrasonic, resistive, optical, acoustic, piezoelectric, PVDF, accelophone, or thermal technologies.

The I/O mechanism 612 may transmit or receive data from a user or another electronic device. The I/O mechanism 612 may include the electronic display 602, a touch sensing input surface, a crown, one or more input buttons (e.g., a graphical user interface "home" button), one or more cameras (including an under-display camera), one or more microphones or speakers, one or more ports such as a microphone port, and/or a keyboard. Additionally or alternatively, the I/O mechanism 612 may transmit electronic signals via a communications interface, such as a wireless, wired, and/or optical communications interface. Examples of wireless and wired communications interfaces include, but are not limited to, cellular and Wi-Fi communications interfaces.

The foregoing description, for purposes of explanation, uses specific nomenclature to provide a thorough understanding of the described embodiments. However, it will be apparent to one skilled in the art, after reading this description, that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art, after reading this description, that many modifications and variations are possible in view of the above teachings.

As described above, one aspect of the present technology may be the gathering and use of data available from various sources, including biometric data. The present disclosure contemplates that, in some instances, this gathered data may include personal information data that uniquely identifies or can be used to identify, locate, or contact a specific person. Such personal information data can include, for example, biometric data and data linked thereto (e.g., demographic data, location-based data, telephone numbers, email addresses, home addresses, data or records relating to a user's health or level of fitness (e.g., vital signs measurements, medication information, exercise information), date of birth, or any other identifying or personal information).

The present disclosure recognizes that the use of such personal information data, in the present technology, can be used to the benefit of users. For example, the personal information data can be used to authenticate a user to access their device, or gather performance metrics for the user's interaction with an augmented or virtual world. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to some health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide data to targeted content delivery services. In yet another example, users can select to limit the length of time data is maintained or entirely prohibit the development of a baseline profile for the user. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in some health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

Although the disclosed embodiments have been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

While various embodiments of the present disclosure have been described above, it should be understood that they have been presented by way of example only, and not limitation. Numerous changes to the disclosed embodiments can be made in accordance with the disclosure herein, without departing from the spirit or scope of the disclosure. Thus, the breadth and scope of the present disclosure should not be limited by any of the above described embodiments. Rather, the scope of the disclosure should be defined in accordance with the following claims and their equivalents.

The invention claimed is:

1. A wearable device, comprising:
a housing;
a display at least partially surrounded by the housing; and
a sensor system housed at least partially in the housing, the sensor system including,
 a first sensor configured to contact a body part of a user and generate a first signal;
 a second sensor configured to sense a mechanical wave in an ambient environment of the wearable device and generate a second signal; and
 a controller configured to,
  generate a resultant signal by removing noise from the first signal using the second signal; and
  determine a health parameter of the user from the resultant signal, wherein: the second sensor comprises a piezoelectric sensor.

2. The wearable device of claim 1, wherein the housing defines a smartwatch.

3. The wearable device of claim 1, wherein the housing defines a smartphone.

4. The wearable device of claim 1, wherein the health parameter of the user includes at least one of: a heart rate; a respiration rate; a blood oxygenation level; a ballistocardiogram; a seismocardiogram; a blood pressure; a blood flow rate; a blood glucose level; or a partial thromboplastin time.

5. The wearable device of claim 1, wherein the sensor system includes a plurality of same types of sensors including the first sensor and the second sensor.

6. A wearable device, comprising:
a housing, including,
 a main body; and
 at least one stem extending from the main body; and
a sensor system housed at least partially in the housing, the sensor system including,
 a first sensor configured to sense an aspect of a body part of a user when the wearable device is worn, the first sensor generating a first signal;
 a second sensor configured to sense a mechanical wave in an ambient environment of the wearable device and generate a second signal; and
 a controller configured to,
  combine the first signal and the second signal; and
  determine a health parameter of the user using the combined first and second signals, wherein:
 the second sensor comprises a polyvinylidene fluoride (PVDF) sensor.

7. The wearable device of claim 6, wherein:
the wearable device is an earbud;
the at least one stem is one stem;
the first sensor is disposed on the main body; and
the second sensor is disposed on the one stem.

8. The wearable device of claim 6, wherein:
the main body includes a glasses frame; and
the at least one stem includes a pair of stems extending from the glasses frame.

9. The wearable device of claim 6, wherein at least one of the first sensor or the second sensor is disposed on the at least one stem.

10. A method of determining a health parameter of a user, the method comprising:
receiving a first signal from a first sensor of an electronic device, the first sensor in contact with a body part of the user;
receiving a second signal from a second sensor of the electronic device, the second sensor spaced apart from the body part, and the second sensor sensing a mechanical wave of an ambient environment of the electronic device;
removing at least a portion of a noise signal from the first signal, using the second signal to form a resultant signal; and
determining the health parameter of the user from the resultant signal,
wherein:
the first sensor comprises a first polyvinylidene fluoride (PVDF) sensor;
the second sensor comprises a second PVDF sensor; and
the removing the at least the portion of the noise signal from the first signal comprises subtracting the second signal from the first signal.

11. The method of claim 10, wherein:
the first PVDF sensor is attached to a back cover of a housing a wearable device; and
the second PVDF sensor is attached to a front cover of the housing of the wearable device.

12. The method of claim 10, further comprising:
generating the second signal at the second sensor in response to receiving the mechanical wave through the ambient environment of the electronic device.

13. The method of claim 10, wherein:
the first PVDF sensor is disposed on an interior surface of a band of a wearable device; and
the second PVDF sensor is disposed on an exterior surface of the band of the wearable device.

14. A wearable device, comprising:
a housing;
a display at least partially surrounded by the housing; and
a sensor system housed at least partially in the housing, the sensor system including,
 a first sensor configured to contact a body part of a user and generate a first signal;
 a second sensor configured to sense a mechanical wave in an ambient environment of the wearable device and generate a second signal; and
 a controller configured to,
  generate a resultant signal by removing noise from the first signal using the second signal; and
  determine a health parameter of the user from the resultant signal, wherein: the second sensor comprises a capacitive gap sensor.

15. A wearable device, comprising:
a housing;
a display at least partially surrounded by the housing; and
a sensor system housed at least partially in the housing, the sensor system including,
 a first sensor configured to contact a body part of a user and generate a first signal;

a second sensor configured to sense a mechanical wave in an ambient environment of the wearable device and generate a second signal; and
a controller configured to,
generate a resultant signal by removing noise from the first signal using the second signal; and
determine a health parameter of the user from the resultant signal, wherein: the second sensor comprises an acoustic sensor.

* * * * *